United States Patent [19]

Arneklev et al.

[11] 3,976,469

[45] Aug. 24, 1976

[54] HALOGENATED KETONES AS HERBICIDE ANTIDOTES

[75] Inventors: Duane R. Arneklev, Antelope, Mont.; Ferenc M. Pallos, Walnut Creek; Edmund Gaughan, Berkeley, both of Calif.

[73] Assignee: Stauffer Chemical Company, Westport, Conn.

[22] Filed: Nov. 25, 1974

[21] Appl. No.: 527,662

Related U.S. Application Data

[63] Continuation of Ser. No. 307,301, Nov. 16, 1972, abandoned.

[52] U.S. Cl. ................................ 71/100; 71/88; 71/93; 71/106; 71/117; 71/118; 71/120; 71/123; 260/476 R; 260/483; 260/487; 260/592; 260/593 R; 260/593 H
[51] Int. Cl.² .......................................... A01N 9/12
[58] Field of Search .............. 71/100, 93, 123, 79

[56] References Cited
UNITED STATES PATENTS

| | | |
|---|---|---|
| 2,913,327 | 11/1959 | Tilles .................................... 71/100 |
| 3,095,299 | 6/1963 | Lockenbaugh ...................... 71/100 |
| 3,131,509 | 5/1964 | Hoffman .............................. 71/79 |
| 3,564,768 | 2/1971 | Hoffman .............................. 71/79 |
| 3,719,466 | 3/1973 | Ahle .................................... 71/88 |

*Primary Examiner*—Glennon H. Hollrah
*Attorney, Agent, or Firm*—Harry A. Pacini

[57] ABSTRACT

Herbicidal compositions comprising an active herbicidal compound and antidote therefor and the methods of use; the antidote compounds correspond to halogenated ketones having the formula

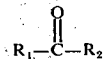

wherein $R_1$ is halocycloalkyl, lower alkyl, lower haloalkyl, phenyl, benzyl and p-tolyl, and $R_2$ is lower haloalkyl, α-halobenzyl, haloacetonyl and haloalkylenecarboalkoxy, provided that when $R_2$ is difluoromonochloromethyl, $R_1$ is other than monofluorodichloromethyl.

40 Claims, No Drawings

HALOGENATED KETONES AS HERBICIDE ANTIDOTES

This is a continuation, of application Ser. No. 307,301, filed Nov. 16, 1972 now abandoned.

BACKGROUND OF THE INVENTION

Among the many herbicidal compounds commercially available, the thiocarbamates alone or admixed with other herbicides, such as the triazines, have reached a relatively high degree of commercial success. These herbicides are immediately toxic to a large number of weed pests at different concentrations varying with the resistance of the weed pests. Some examples of these compounds are described and claimed in the U.S. Pat. No. 2,913,327, 3,037,853, 3,175,897, 3,185,721, 3,198,786 and 3,582,314.

It has been found in practice that the use of these thiocarbamates as herbicides on crops sometimes causes serious injuries to the crop plant. When used in the recommended amounts in the soil to control many broadleaf weeds and grasses, serious malformation and stunting of the crop plants result. This abnormal growth in the crop plants results in loss of crop yield. Previous attempts to overcome this problem involves the treatment of the crop seed with certain antagonistic agents prior to planting, see U.S. Pat. No. 3,131,509 and 3,564,768. These antagonistic agents have not been notably successful. The aforementioned patent specifically exemplifies the treatment of seeds employing compounds of a different chemical class not suggestive of the present invention.

DESCRIPTION OF THE INVENTION

It has been discovered that plants can be protected against injury by various herbicides, for example, the thiocarbamate-type herbicides, alone or mixed with other herbicidal compounds and/or the tolerance of the plants can be substantially increased to the active compounds of the above-noted U.S. Patents by adding to the soil an antidote compound corresponding to the following formula

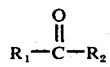

wherein $R_1$ is halocycloalkyl, lower alkyl, lower haloalkyl, phenyl, benzyl and p-tolyl and $R_2$ is lower haloalkyl, α-halobenzyl, haloacetonyl and haloalkylenecarboalkoxy, provided that when $R_2$ is difluoromonochloromethyl, $R_1$ is other than monofluorodichloromethyl.

In the description of the halogenated ketones as compounds useful in the herbicidal antidote method of this invention, the following embodiments are intended for the various groups: The term halo preferably refers to fluoro, chloro and bromo substitution in mono, di, tri, tetra and per substitution. Halo also is intended to relate to mixed halogen substitution, such as in dichloromonofluoromethyl, and the like. Cycloalkyl preferably includes those members containing from 3 to 6 carbon atoms, inclusive, such as cyclopropyl, cyclobutyl, cyclopentyl and cyclohexyl. The term lower alkyl preferably includes those members containing from 1 to 4 carbon atoms, inclusive, in both branched and straight chain configuration; the term halo can be used as a prefix with these groups as defined herein, for example, dichloromethyl, chlorodifluoromethyl, trichloromethyl, 1,-bromopropyl and the like. The term haloalkylenecarboalkoxy preferably includes those members having a total of 3 to 8 carbon atoms, inclusive.

As an alternative mode of action, the compounds of this invention may interfere with the normal herbicidal action of the thiocarbamate-type and other herbicides to render them selective in their action. Whichever mode of action is present, the corresponding beneficial and desirable effect is the continued herbicidal effect of the thiocarbamate or other herbicide with the accompanying decreased herbicidal effect on desired crop species. This advantage and utility will become more apparent hereinafter.

Therefore, the terms herbicide, antidote or antidotal amount, is meant to describe that effect which tends to counteract the normal injurious herbicidal response that the herbicide might otherwise produce. Whether it is to be termed a remedy, interferant, protectant, or the like, will depend upon the exact mode of action. The mode of action is varied, but the effect, which is desirable, is the result of the method of treating the soil in which a crop is planted. Hitherto, there have been no systems which have been satisfactory for this purpose.

The compounds of this invention represented by the above formula, can be prepared by several different procedures depending upon the starting materials and desired products.

Many of the compounds of the instant method are known in the prior art. If the compound was not available from a commercial source, it was prepared by normal halogenation processes. For example, some compounds were brominated or chlorinated by mixing bromine or chlorine with the unhalogenated starting material. An inert solvent such as methylene chloride was used to facilitate the reaction and the work-up procedure. For more vigorous halogenation conditions it was necessary to employ a catalyst such as aluminum trichloride. In all reactions, normal work-up procedures were used to recover the final product.

The following examples are illustrative of the preparation of some of the compounds of the instant invention.

EXAMPLE I

Preparation of 3-Bromo-2,4-pentanedione.

Pentanedione (50 g., 0.5 mole) was dissolved in 100 ml. methylene chloride with 0.2 g. aluminum trichloride present. Bromine (80 g., 0.5 mole) was added to the solution while stirring. After the addition was complete, stirring was continued for about 1 hour. The solvent was removed in vacuo. There was obtained 69.5 g. of the title compound, a dark red oil.

EXAMPLE II

Preparation of α,α-dichloroethylbenzoylacetate.

Ethylbenzoylacetate, 104 g. (0.54 mole), was treated with chlorine gas in 300 ml. carbon tetrachloride as the solvent. The absorption of the chlorine gas is a spontaneous and mildly exothermic reaction. A water bath was used to keep the temperature between 30°–35°C. When the second equivalent of chlorine is to be added, the reaction decreased. A warm water bath was needed to aid the addition reaction to continue to completion. The solvent was removed in vacuo. After fractional distillation at 3mm/Hg., there was obtained as the main fraction 121 g. of the title compound, b.p. 137°C./3mm/Hg., $n_D^{25} = 1.5286$.

The following is a table of compounds which are within the scope of the present invention. Compound numbers have been assigned to them and are used for identification throughout the balance of the specification.

TABLE I $$R_1-\overset{\overset{O}{\|}}{C}-R_2$$

| COMPOUND NUMBER | $R_1$ | $R_2$ | m.p. °C., b.p. °C., or $n_D^{30}$ |
|---|---|---|---|
| 1 | 4-Cl-cyclohexyl | $CH_2Cl$ | 101–102°C. m.p. |
| 2 | phenyl | $CHBr_2$ | 33–35°C. m.p. |
| 3 | methyl | $CHCl_2$ | 1.4365 |
| 4 | phenyl | $CBr_2CH_3$ | 1.5765 |
| 5 | $CCl_3$ | $CHCl_2$ | 192°C. b.p. |
| 6 | phenyl | $CH_2Br$ | 49°C. m.p. |
| 7 | p-$CH_3$-phenyl | $CH_2Br$ | 52°C. m.p. |
| 8 | $Cl_2CH$ | $CHCl_2$ | 1.4946 |
| 9 | $CF_2Cl$ | $CF_2Cl$ | colorless liquid |
| 10 | $CH_3$ | $CHBr\overset{\overset{O}{\|}}{C}CH_3$ | dark red oil |
| 11 | phenyl-$CH_2$ | phenyl-CHBr | yellow liquid |
| 12 | phenyl | $CCl_2\overset{\overset{O}{\|}}{C}OC_2H_5$ | 1.5286 |
| 13 | phenyl | $CHBrCH_2CH_3$ | yellow oil |
| 14 | $CH_3$ | $CHBrCH_3$ | yellow liquid |

The compounds of this invention were employed in effective herbicidal antidote compositions comprising thiocarbamates and triazines in combination with antidote compounds described hereinabove. They were tested in the following manner.

Corn Seed Treatment Test

Small flats were filled with Felton loamy sand soil. Soil incorporated herbicides were applied at this time. The soil from each flat was placed into a five-gallon cement mixer where the soil was mixed as the herbicides were applied using a predetermined amount of a stock solution containing 936 mg. of 75.5% active ingredient to 100 ml. of water. One ml. of stock solution was applied to the soil in a volumetric pipet for each pound of herbicide desired. One ml. of stock solution contained 7 mg. of herbicide which equals one pound per acre when applied to the soil in the flats. After the herbicide incorporation, the soil was placed back into the flats.

Flats of herbicide-treated and untreated soil were then ready to be planted. A pint sample of soil was removed from each flat and placed next to each flat for later use in covering up the seeds. The soil was leveled and rows one-half inch deep were made for planting seeds. Alternating rows of treated and untreated crop seeds were sown. In each test, six PAG 344T or DeKalb XL 374 field corn seeds were planted in each row. Rows were approximately 1½ inches apart in the flat. Seeds were treated by placing 50 mg. of the antidote compound with 10 grams of corn seed (0.5% w/w) in a suitable container and shaking them until the seeds were uniformly covered with the compound. Antidote compounds were also applied as liquid slurries and powders or dusts. In some cases, acetone was used to dissolve powdered or solid compounds so they could be more effectively applied to the seeds.

After the flats were seeded, they were covered with the one pint of soil which had been removed just prior to planting. Flats were placed on greenhouse benches where temperatures ranged from 70°–90°F. Flats were watered by sprinkling as needed to assure good plant growth. Percent control ratings were taken two, three and four weeks after the treatments were applied.

In each test, the herbicide was applied alone, in combination with the seed protectant, and the seed protectant was applied alone to check for phytotoxicity. The untreated adjacent row was employed to observe any beneficial lateral movement of the antidote compound through the soil. The degree of the effect was noted by comparison with the control. The results of these tests are tabulated in Table II.

TABLE II

Per Cent Injury to Corn from EPTC*
Seed Treatment Test

| COMPOUND NUMBER | Per Cent Injury, 2 weeks | |
|---|---|---|
| | Treatment Seed (0.5% w/w) | Untreated Seed Adjacent Row |
| 1 | 40 | 97 |
| 2 | 20 | 98 |
| 3 | 20 | 35 |
| 4 | 0 | 73 |
| 5 | 20 | 80 |
| 6 | 60 | 75 |
| 7 | 60 | 80 |
| 8** | 30 | 60 |
| EPTC 6E Untreated Seed | — | 70 |
| | | 80 (4 weeks) |

*=S-ethyl dipropylthiocarbamate 6E: 6 lb/A pre-plant incorporat
**=Seed treatment 0.05% w/w Procedure: Multicrop Antidote Screen Plastic flats were filled with Felton loamy sand soil. Since a variety of grass and broadleaf crops were used in these tests, EPTAM (EPTC) was incorporated at ½ and 5 lb/A, while a constant rate of 5 lb/A of the additive was used. EPTAM (EPTC) and the herbicide additive were applied separately by pipetting measured amounts of the apprpriate stock solutions into the soil during incorporation in a 5 gallon rotary cement mixer. Stock solutions for EPTAM were prepared as follows:

A. ½ lb/A: 670 mg. of EPTC 6E (75.5% a.i.) was diluted with 500 ml. of deionized water so that 2 ml. equals ½ lb/A/plastic flat.

B. 5 lb/A: 6700 mg. of EPTC 6E (75.5%) was diluted with 500 ml. of deionized water so that 2 ml. equals 5 lb/A/plastic flat.

Additive stock solutions were prepared by diluting 102 mg. of technical material with 10 ml. of acetone 1% Tween 20 (polyoxyethylene sorbitan monolaurate) so that 2 ml. equals 5 lb/A/flat.

After the soil was treated with both herbicide and additive the soil was transferred from the mixer back into the flat where it was then prepared for seeding. The initial step in preparation was to remove a one pint sample of soil from each flat to be retained and used to cover the seeds after planting. The soil was then leveled and rows one-quarter inch deep were made in each flat. Flats treated with 5 lb/A of EPTAM were seeded to DeKalb XL-44 corn (Zea maize), US H9 sugarbeets (*Beta vulgare*), small seeded gray striped sunflower (*Helianthus annus*), Acala cotton (*Gossypium hirsutum*), Brag soybeans (*Glycine max*) and oilseed rape (*Brassica napus*). Flats treated with 1/2 lb/A of EPTAM were seeded to red oats (*Avena byzantina*), R-10 milo (*Sorgum vulgare*), Fremont HRS wheat (*Triticum aestivum*), giant foxtail (*Seteria feberii*), Calrose rice (*Oryza sativa*) and Blue Mariate barley (*Hordeum vulgare*). Seeds were then covered with the pint soil sample removed prior to seeding.

The flats were then placed on greenhouse benches where temperatures were maintained between 70°–90°F. The soil was watered by sprinkling to assure good plant growth.

Injury ratings were taken 2 and 4 weeks after the treatments were applied. Soil treated with EPTAM alone at ½ or 5 lb/A was included to provide a basis for determining the amount of injury reduction provided by the herbicide antidotes. The per cent protection of various representative crops is reported in Table III. The per cent protection is determined by a comparison with flats not treated with the candidate antidote.

TABLE III

| COMPOUND NUMBER | Herbicide | Multicrop Screen Results Per Cent Protection Rate of Herbicide lb/A | Crop | % Protection (2 weeks) |
|---|---|---|---|---|
| 2* | EPTC | 0.5 | sorghum | 85 (4 weeks) |
|  |  | 3.0 | corn | 100 |
| 9 | EPTC | 3.0 | corn | 100 |
|  |  | 3.0 | soybeans | 80 (4 weeks) |
| 10 | EPTC | 3.0 | corn | 100 |
|  |  | 3.0 | soybeans | 60 (4 weeks) |
| 11 | EPTC | 3.0 | corn | 50 |
| 12 | EPTC | 3.0 | corn | 100 |
| 2 | Atrazine** | 2.0 | cotton | 40 (3 weeks) |
| 9 | Atrazine | 2.0 | cotton | 50 (3 weeks) |
| 13 | EPTC | 0.5 | sorghum | 67 (4 weeks) |
| 14 | EPTC | 0.5 | rice | 86 (4 weeks) |
|  |  | 5.0 | soybeans | 47 (4 weeks) |
|  |  | 5.0 | corn | 52 (4 weeks) |

*=Antidote used at 10 lb/A
**=2-chloro-4-ethylamino-6-isopropylamino-s-triazine

The antidote compounds and compositions of the present invention can be used in any convenient form. Thus, the antidote compounds can be formulated into emulsifiable liquids, emulsifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not affect the herbicidal activity of the herbicides.

The amount of antidote compound present can range between about 0.001 to about 15 parts by weight of antidote compound described herein per each part by weight of herbicide. The exact amount of antidote compound will usually be determined on economic ratios for the most effective amount usable. It is understood that a non-phytotoxic quantity of antidote compound will be employed in the herbicidal compositions described herein.

The herbicides indicated in the tables and elsewhere are used at rates which produce effective control of undesirable vegetation. The range of rates employed herein produce representative results within the recommended amounts set forth by the supplier. Therefore, the weed control in each instance is commercially acceptable within the desired or recommended amount.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention are prevention of injury to a desired crop species in the presence of a specific compound or combination may be achieved. The beneficial plant species which can be protected by this method is not intended to be limited by the specific crops employed in the examples.

The herbicidal compounds employed in the utility of this invention are active herbicides of a general type. That is, the members of the classes are herbicidally effective against a wide range of plant species with some degree of discrimination between desirable and undesirable species. The method of controlling vegetation comprises applying an herbicidally effective amount of the hereindescribed herbicidal compounds to the area or plant locus where control is desired. The compositions as set forth in this invention include those wherein the preferred active herbicidal compound is selected from S-ethyl dipropylthiocarbamate; S-ethyl diisobutyl thiocarbamate, S-propyl dipropyl thiocarbamate, S-2,3,3-trichloroallyl-diisopropyl thiocarbamate, S-ethyl cyclohexyl ethyl thiocarbamate, 2-chloro-2',6'-diethyl-N-(methoxymethyl)acetanilide, S-ethyl hexahydro-1H-azepine-1-carbothioate, 2-chloro-N-isopropylacetanilide, N,N-diallyl-2-chloroacetamide, S-4-chlorobenzyl diethyl thiocarbamate, 2-chloro-4-ethylamino-6-isopropylamino-s-triazine, 2-chloro-4,6-bis(ethylamino)-s-triazine, 2(4-chloro-6-ethylamine-s-triazine-2-ylamino)-2-methylpropionitrile, 2-chloro-4-cyclopropylamino-6-isopropylamino-s-triazine, 2,4-dichlorophenoxyacetic acid, its esters and salts, and 3-(3,4-dichlorophenyl)-1,1-dimethylurea and combinations thereof.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants" it is meant germinant seeds, emerging seedlings, and established vegetation, including the roots and above-ground portions.

What is claimed is:

1. The method of reducing injury to corn plants injured by thiocarbamate herbicides comprising applying to the corn seeds prior to planting a non-phytotoxic antidotally effective amount of a compound corresponding to the formula

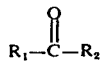

wherein $R_1$ is halocycloalkyl in which halo is fluoro, chloro or bromo and containing from 3 to 6 carbon atoms, inclusive, lower alkyl containing from 1 to 4 carbon atoms, inclusive, lower haloalkyl in which halo is fluoro, chloro or bromo and containing from 1 to 4 carbon atoms, inclusive, phenyl, benzyl, and p-tolyl; $R_2$ is lower haloalkyl in which halo is fluoro, chloro or bromo and containing from 1 to 4 carbon atoms, inclusive, α-halobenzyl in which halo is fluoro, chloro or bromo, haloacetonyl in which halo is fluoro, chloro or bromo, and haloalkylenecarboalkoxy in which halo is fluoro, chloro or bromo and having a total of 3 to 8 carbon atoms, inclusive, provided that when $R_2$ is difluoromonochloromethyl, $R_1$ is other than monofluorodichloromethyl.

2. The method according to claim 1 in which $R_1$ is lower alkyl and $R_2$ is haloalkyl.

3. A method according to claim 2 in which $R_1$ is methyl and $R_2$ is dichloromethyl.

4. A method according to claim 2 in which $R_1$ is methyl and $R_2$ is 1-bromoethyl.

5. The method according to claim 1 in which $R_1$ is phenyl and $R_2$ is haloalkyl.

6. A method according to claim 5 in which $R_2$ is dibromomethyl.

7. A method according to claim 5 in which $R_2$ is 1,1-dibromoethyl.

8. A method according to claim 5 in which $R_2$ is bromomethyl.

9. A method according to claim 5 in which $R_2$ is 1-bromopropyl.

10. A method according to claim 1 in which $R_1$ is 4-chlorocyclohexyl and $R_2$ is chloromethyl.

11. The method according to claim 1 in which $R_1$ is lower haloalkyl and $R_2$ is lower haloalkyl.

12. A method according to claim 11 in which $R_1$ is trichloromethyl and $R_2$ is dichloromethyl.

13. A method according to claim 11 in which $R_1$ is dichloromethyl and $R_2$ is dichloromethyl.

14. A method according to claim 11 in which $R_1$ is chlorodifluoromethyl and $R_2$ is chlorodifluoromethyl.

15. A method according to claim 1 in which $R_1$ is phenyl and $R_2$ is dichloromethylenecarboethoxy.

16. A method according to claim 1 in which $R_1$ is lower alkyl and $R_2$ is haloacetonyl.

17. A method according to claim 16 in which $R_1$ is methyl and $R_2$ is 1-bromoacetonyl.

18. A method according to claim 1 in which $R_1$ is benzyl and $R_2$ is α-bromobenzyl.

19. A method according to claim 1 in which $R_1$ is p-tolyl and $R_2$ is lower haloalkyl.

20. A method according to claim 19 in which $R_2$ is bromomethyl.

21. The method of reducing injury to crops selected from corn, sorghum, soybeans, cotton and rice injured by thiocarbamate herbicides comprising applying to the soil in which said crops are to grow and in which said herbicides are to be applied a non-phytotoxic antidotally effective amount of a compound corresponding to the formula

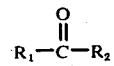

wherein $R_1$ is halocycloalkyl in which halo is fluoro, chloro or bromo and containing from 3 to 6 carbon atoms, inclusive, lower alkyl containing from 1 to 4 carbon atoms, inclusive, lower haloalkyl in which halo is fluoro, chloro or bromo and containing from 1 to 4 carbon atoms, inclusive, phenyl, benzyl, and p-tolyl; $R_2$ is lower haloalkyl in which halo is fluoro, chloro or bromo and containing from 1 to 4 carbon atoms, inclusive, α-halobenzyl in which halo is fluoro, chloro or bromo, haloacetonyl in which halo is fluoro, chloro or bromo, and haloalkylenecarboalkoxy in which halo is fluoro, chloro or bromo and having a total of 3 to 8 carbon atoms, inclusive, provided that when $R_2$ is difluoromonochloromethyl, $R_1$ is other than monofluorodichloromethyl.

22. The method according to claim 21 in which $R_1$ is lower alkyl and $R_2$ is haloalkyl.

23. The method according to claim 22 in which $R_1$ is methyl and $R_2$ is dichloromethyl.

24. The method according to claim 22 in which $R_1$ is methyl and $R_2$ is 1-bromoethyl.

25. The method according to claim 21 in which $R_1$ is phenyl and $R_2$ is haloalkyl.

26. The method according to claim 25 in which $R_2$ is dibromomethyl.

27. The method according to claim 25 in which $R_2$ is 1,1-dibromoethyl.

28. The method according to claim 25 in which $R_1$ is bromomethyl.

29. The method according to claim 25 in which $R_2$ is 1-bromopropyl.

30. The method according to claim 21 in which $R_1$ is 4-chlorocyclohexyl and $R_2$ is chloromethyl.

31. The method according to claim 21 in which $R_1$ is lower haloalkyl and $R_2$ is lower haloalkyl.

32. The method according to claim 31 in which $R_1$ is trichloromethyl and $R_2$ is dichloromethyl.

33. The method according to claim 31 in which $R_1$ is dichloromethyl and $R_2$ is dichloromethyl.

34. The method according to claim 31 in which $R_1$ is chlorodifluoromethyl and $R_2$ is chlorodifluoromethyl.

35. The method according to claim 21 in which $R_1$ is phenyl and $R_2$ is dichloromethylenecarboethoxy.

36. The method according to claim 21 in which $R_1$ is lower alkyl and $R_2$ is haloacetonyl.

37. The method according to claim 36 in which $R_1$ is methyl and $R_2$ is 1-bromoacetonyl.

38. The method according to claim 21 in which $R_1$ is benzyl and $R_2$ is α-bromobenzyl.

39. The method according to claim 21 in which $R_1$ is p-tolyl and $R_2$ is lower haloalkyl.

40. The method according to claim 39 in which $R_2$ is bromomethyl.

* * * * *